United States Patent [19]
Levine et al.

[11] Patent Number: 5,593,848
[45] Date of Patent: Jan. 14, 1997

[54] TARGET COMPONENT ASSAY UTILIZING SPECIFIC GRAVITY-ALTERING LIPOSOMES

[75] Inventors: Robert A. Levine, Guilford; Stephen C. Wardlaw, Old Saybrook, both of Conn.; Rodolfo Rodriguez, Owings Mills; Judith Britz, Laurel, both of Md.; Thomas J. Mercolino, Pleasanton, Calif.

[73] Assignee: Becton Dickinson and Company, Franklin Lakes, N.J.

[21] Appl. No.: 335,310

[22] Filed: Nov. 7, 1994

Related U.S. Application Data

[63] Continuation of Ser. No. 841,976, Feb. 25, 1992, abandoned.

[51] Int. Cl.$^6$ .................. G01N 33/533; G01N 33/536; G01N 33/537

[52] U.S. Cl. .................. 435/7.24; 435/7.22; 435/7.23; 435/7.25; 435/7.92; 436/528; 436/538; 436/829

[58] Field of Search .................. 435/7.22, 7.23, 435/7.24, 7.25, 7.92; 436/528, 538, 829

[56] References Cited

U.S. PATENT DOCUMENTS

| | | | |
|---|---|---|---|
| 3,862,303 | 1/1975 | Anderson | 436/531 |
| 4,027,660 | 6/1977 | Wardlaw et al. | 128/771 |
| 4,342,739 | 8/1982 | Kakimi et al. | 435/7.9 |
| 4,623,618 | 11/1986 | Rokugawa | 435/6 |
| 4,978,625 | 12/1990 | Wagner | 436/518 |
| 5,011,771 | 4/1991 | Bellet et al. | 435/7.94 |
| 5,017,472 | 5/1991 | Bankert et al. | 435/7.25 |

FOREIGN PATENT DOCUMENTS

| | | |
|---|---|---|
| 0276165 | 7/1988 | European Pat. Off. . |
| 0035267 | 2/1985 | Japan . |
| 2239197 | 6/1991 | United Kingdom . |

OTHER PUBLICATIONS

Lyon et al, Molecular and Biochemical Parasitology 36:77–86 Aug. 1989.
Cole et al, Biochemical and Biophysical Research Communications 170(1):288–295, Jul. 1990.
Goormaghtigh, Analytical Biochemistry 159:122–131 1986.
Foutain, Biochimica et Biophysica Acta 596:420–425 1980.

*Primary Examiner*—James C. Housel
*Assistant Examiner*—Nancy J. Parsons
*Attorney, Agent, or Firm*—William W. Jones

[57] ABSTRACT

An improved assay of target components in a sample utilizes specific gravity-altering particles which are attached to the target components by specific antibodies. The attached specific gravity-altering particles are preferably liposomes which will buoy or sink the targets to a common level in the specimen sample when the latter has been centrifuged in a transparent tube. The liposomes can provide an accentuated and more pronounced indication of the presence of the targets in the sample due to their ability to contain many multiples of fluorescent or non-fluorescent dye molecules with minimal steric interference with the attached antibodies' binding ability.

5 Claims, 1 Drawing Sheet

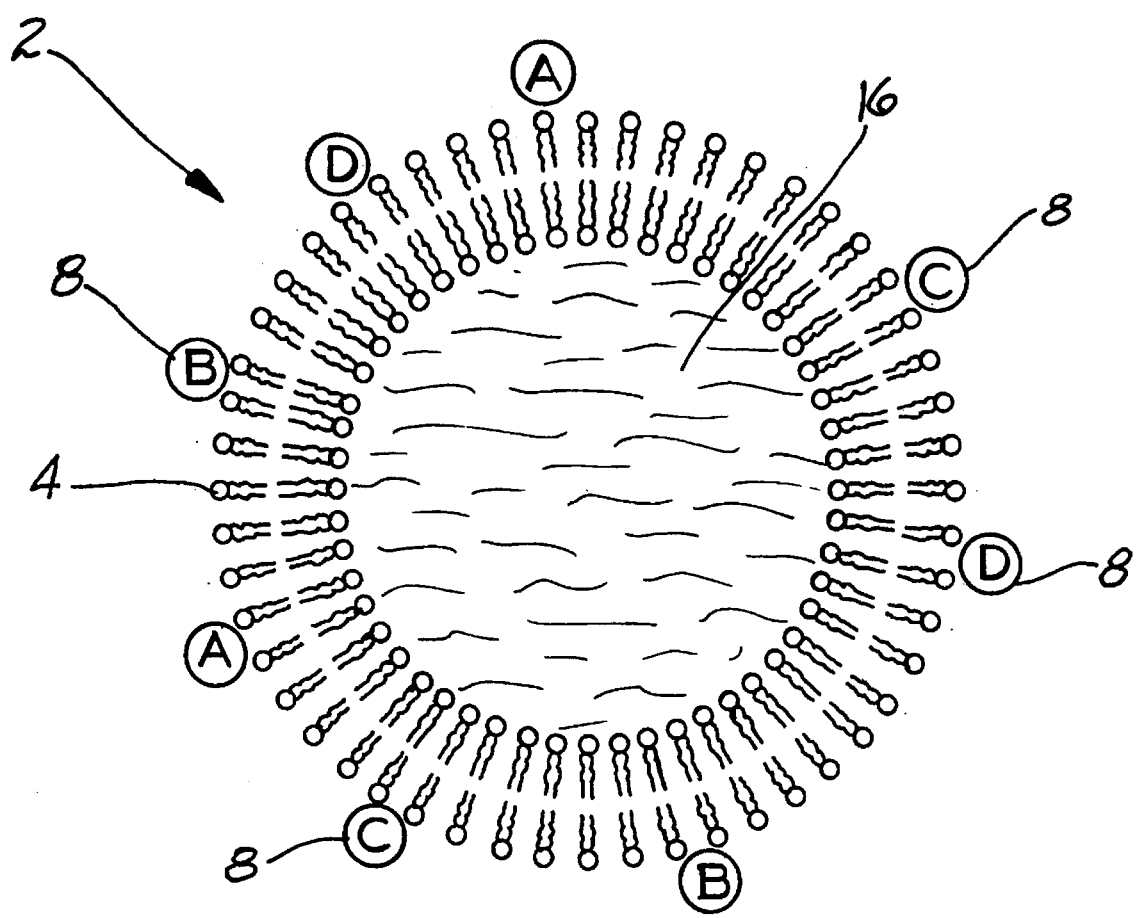

TARGET COMPONENT ASSAY UTILIZING SPECIFIC GRAVITY-ALTERING LIPOSOMES

This is a continuation of U.S. Ser. No. 07/841,976, filed Feb. 25, 1992, now abandoned.

This invention relates to the assaying of target components of specimen samples. More particularly, this invention relates to the detection and/or quantification of target cells, particles or organisms, hereinafter referred to as "targets", in biological specimen samples by simultaneous modification of the specific gravity and highlighting or tagging of the targets.

U.S. Pat. No. 4,181,609 granted Jan. 1, 1980 to S. C. Wardlaw et al discloses a blood analysis procedure wherein certain blood cells (reticulocytes) are densified so that a clear cell interface is formed in a centrifuged blood sample. Thus the alteration of the natural specific gravity of the reticulocytes results in an improved blood test. U.S. Pat. No. 4,332,785 granted Jan. 1, 1982 to Allen et al discloses a specific procedure which uses fluorescent antibodies to tag reticulocytes in a quantitative analysis of reticulocytes in a blood sample; and U.S. Pat. No. 4,591,570 granted May 27, 1986 to Chang discloses the use of a number of different antibodies spotted on a carrier to capture a plurality of different antigens in an immunoassay procedure. The prior art does not, however, disclose a general procedure which involves altering the specific gravity of a number of different specimen sample components in order to congregate the altered components in a centrifuged specimen sample, and to tag the components so as to render them readily identifiable.

This invention relates to an improved assay of target components of specimen samples which involves selectively attaching observably differentiated liposomes to the respective sample target components. The liposomes are attached to the specimen components by means of antibodies affixed to the surface of the liposomes. The antibodies will include at least one antibody which is specific to a surface antigen known to occur on the sample target component. Different antibodies can be concurrently attached to the surface of a single liposome, thus the assay can be specific to each of many different targets. The differentiation of the liposomes is preferably provided by a visible or machine-readable distinguishing marker encapsulated inside of the liposomes, or incorporated in the phospholipid bilayer. The distinguishing marker can be a visible dye; a machine readable dye; a radioactive emitter; or the like.

Liposomes are microscopic, spherical man-made structures composed predominently of phospholipids. A liposome may consist of one or more lamellar phospholipid vesicles which form a closed spherical shell which can be loaded or filled with a material such as a liquid, or the like. Since liposomes have a size in the range of 150–250 nm, and the average thickness of a lipid membrane is 2.5 nm, it is apparent that the specific gravity of the liposome is determined primarily by the density of the encapsulated substance, i.e., the dye, or indicator, and the buffer or carrier medium. Methods for preparing and utilizing liposomes are disclosed in "Liposomes: Diagnostic and Therapeutic Applications", by James O'Connell, in the December 1988 issue of Medical Device and Diagnostic Industry, at pages 31–36.

This invention relates to the use of specially prepared liposomes to separate and highlight different constituents of a specimen sample. The liposomes will be filled or loaded with a tagging or highlighting material, such as a liquid containing a visible or machine readable colorant, or some other sensable component. The filler material will have a predetermined specific gravity which will thus define the specific gravity of the liposomes. The outer surface of the liposomes will have attached thereto one or more different antibodies, which will be specific to different surface antigens known to exist on different targets in different samples to be tested. Thus, for example, the liposomes could be filled with a fluorescing liquid having a specific gravity of 1.5, and could have attached thereto antibodies A, B, C, and D which would be specific to surface antigens a, b, c, and d. These surface antigens would be antigens known to exist on one or more targets in different specimen samples which could be assayed, either qualitatively or quantitatively. Thus a single assaying medium could be used to assay several different samples, in the following manner, by way of example. It is also possible to use different liposomes A–D, each with its own specific gravity to assay the aforesaid a–d surface antigens simultaneously.

It will be appreciated from the foregoing general example, that the invention has vast application in the medical field for diagnosing, and/or quantifying, procedures. One need merely know the specific gravity of the constituent to be assayed; and what surface antigens it possesses. Once these facts are known, a liposome can be created to tag the constituent and to congregate it in the sample in which it resides. The antibodies used can be polyclonal or monoclonal antibodies.

It is therefore an object of this invention to provide an improved procedure for assaying a specimen sample for a particular target constituent residing therein.

It is a further object of this invention to provide a procedure of the character described which may alter the specific gravity of the target constituent and also highlight the target constituents so as to render them detectable in the sample.

It is another object of this invention to provide a target constituent highlighting material which can be made simultaneously specific to many different target constituents.

It is yet another object of this invention to provide a procedure of the character described which may quantitatively and/or qualitatively assay the target constituents in the sample.

These and other objects and advantages of the invention will become more readily apparent from the following detailed description of several preferred embodiments thereof when taken in conjunction with the accompanying drawing which is a schematic view of a liposome modified for use in connection with this invention.

Referring to the drawing, there is shown a unilamellar vesicle liposome denoted generally by the numeral 2. The membrane 4 of the vesicle 2 is very thin, about 40 A in thickness and yet encapsulates a proportionally large volume. The interior of the vesicle contains a marker liquid 6 such as a dye, or the like, which may be dispersed in a carrier fluid. The antibodies 8 are attached to the exterior of the membrane 4. As an example, there are shown the four different antibodies A, B, C and D on the exterior of the membrane 4. As previously noted, hundreds (or thousands) of different antibodies can actually be attached to each vesicle, if so desired. The antibodies are believed to be movable over the exterior of the vesicle 2 so that no particular orientation of the vesicle is needed to obtain the desired tagging of the target constituents. It will be noted that, due to the vastly greater proportion of encapsulated marker 6 to membrane 4 in the vesicle, the specific gravity of the marker 6 and/or its carrier determines the specific gravity of the vesicle 2.

The vesicles 2 can be produced by any conventional method with the marker 6 being encapsulated during production of the vesicles, as described in the above-identified O'Connell reference. Szoka and Papahadjopoulos describe several methods for attaching antibodies to liposomes in their article: "Liposomes: Preparation and Characterization", pages 69–82, *From Physical Structure to Therapeutic Applications*, Elsevier/North Holland Biomedical Press 1981. For example, the liposomes can be prepared by encapsulating 5 mM fluorescein sulfonic acid marker dissolved in 5 mM EDTA buffer carrier, having a pH of 4.5. Antibodies can be coupled to the intact liposomes through a Schiff base which is reduced at neutral or alkaline pH to a stable amide by the sodium cyanoborohydride method described by Fiddler and Gray in Vol. 86 of *Analytical Biochemistry* at pages 716–724. This procedure utilizes periodate oxidation of liposomes containing 10 mole percent lactosylcerebroside or mixed brain gangliosides. The oxidation step is carried out either under acid (pH 5.5) or alkaline (pH 8.4) conditions. The time of periodate oxidation at pH 5.5 must be carefully controlled to prevent periodate from entering the liposomes. A subsequent reduction step with sodium cyanoborohydride is done at neutral pH. Vesicle integrity is maintained during the reaction as indicated by the fact that entrapped contents do not leak out of the liposomes nor are entrapped periodate-cleavable components oxidized. Protein coupling is efficient with the aforesaid technique. Protein-to-protein crosslinking or liposome aggregation are not serious problems with the aforesaid method.

This invention can be used in the quantification of reticulocytes in a sample of whole blood. Reticulocytes are young erythrocytes, and the quantitative measurement of reticulocytes in a sample of blood can be used to determine the body's production rate of red blood cells. Reticulocyte quantification is important in determining the cause of anemia, and may also be used to ascertain the presence of "compensated blood loss" i.e., a normal amount of red blood cells which is present only because of an abnormally high rate of red blood cell production. Such compensated blood loss may be an early indication of the presence of gastrointestinal bleeding due to malignancy or other causes. Reticulocytes have the surface antigen transferrin to which antitransferrin antibodies can bind. The reticulocyte population of a sample of whole blood can thus be quantified by attaching the antitransferrin receptor antibodies to the membrane of liposomes containing a liquid colorant such as a dye or fluorescent colorant which has a specific gravity different from the reticulocytes and mature red cells. The tagging liposomes are then mixed with the blood sample to the extent needed to bind all of the reticulocytes in the blood sample. The mixture is then placed in a blood analyzing tube of the invention disclosed in U.S. Pat. No. 4,027,660 granted to S. C., Wardlaw et al and quantified in accordance with the procedures described therein.

This invention can also be used to detect and quantify T-lymphocytes and their subsets: in a subject's blood. T-lymphocytes are a subgroup of lymphocytes that are mediators of cellular immunity; and B-lymphocytes are mediators of humoral immunity (antibody producers).

A discussion of lymphocytes reactivity to specific antigens in blood is contained in U.S. patent application Ser. No. 07/340,248 filed Apr. 19, 1989 by Robert A, Levine and Stephen C. Wardlaw. Activated lymphocytes, (lymphoblasts) possess surface activation antigens such a transferrin receptor; HLA-Dr; Leu-23 and the like. In order to detect the lymphoblasts, antibodies specific to one of the aforesaid lymphocyte antigens are attached to liposomes into which a suitable marker is incorporated. The tagging liposomes are then mixed with a blood sample for a time suitable to allow binding of the liposomes to any lymphoblasts which may be present in the blood sample. The mixture is then drawn into a blood analyzing tube of the type disclosed in U.S. Pat. No. 4,027,660 and tested in accordance with the procedures described therein.

Since the cells being assayed are white cells, the marker dye will preferably be selected with a specific gravity which is different from the white cells so as to cause any tagged lymphoblasts to layer out away from the rest of the white cells, or in a localized band in the white cells. The liposomes used in the lymphocyte-subset selection for T-lymphocytes have a density of less than 1.017 gm/ml. Lymphocytes have a mean density of 1.06 gm/ml and density range of 1.055 to 1.070 gm/ml. Therefore, the liposomes used are able to decrease the density of the target T-lymphocytes causing them to rise to the top of the lymphocyte layer.

The following is a example of use of the invention to the detection of T-lymphocytes in a blood sample. A marker composition including 25 μl of an undiluted 55-2/LEU-1 antibody coupled to liposomes loaded with a fluorescein (fluorescent) dye having a specific gravity of less than 1.017 was added to 1 ml of EDTA venous blood, and to that mixture 25 μl of undiluted 0.42 g/10 ml stock solution of sodium fluoride was added. The sodium fluoride produces a sharper separation of the non-fluorescent and fluorescent components of the lymphocyte cell bands. To the aforesaid mixture 50 μl of undiluted 1.1 g/10 ml of a stock solution of potassium oxalate was added to give a sharper red cell/granulocyte separation as described in the prior art referred to first above. The resultant mixture was allowed to incubate for five minutes, after which the mixture was centrifuged to separate the various cell types in a capillary, or other, transparent tube containing a plastic float which expands the various cells in the sample. Using the aforesaid technique, a distinct band of fluorescent lymphocytes was formed in the white cell layer. This band was quantified by measuring its axial extent in the tube. The resulting value was an indication of the circulating T-lymphocyte cells in the blood. When dyes or stains having a different specific gravity are used, the tagged cells can be made to settle out elsewhere in the centrifuged blood sample.

The invention can also be used to assay other cells, particles or organisms in biological fluid samples. The presence of abnormal amounts of Beta-amyloid protein (BAP) is known to occur in the brain, skin and colonic mucosa of patients suffering from Alzheimer's disease, a degenerative neurologic disease; and in older patients with Down's Syndrome, a congenital disorder also known as trisomy 21. BAP has not been detectable in serum to date. The presence of BAP in white blood cells of the lymphocyte type, or other types, may be detected by using liposome-attached antibodies directed against surface antigens on BAP, which antigens are exposed on the surface of the circulating cells which are producing BAP.

With respect to detection of organisms in biological fluid samples, malarial protozoa are generally intracellular organisms located within the red blood cells and are not generally detectable by immunologic means since antibodies are not able to penetrate the red blood cell membrane in intact living cells. Malarial protozoa of the falciparum type produce characteristic red blood cell changes in infected red blood cells. There is a vital need to distinguish falciparum malaria from non-falciparum malaria since the former is often fatal and often resistant to commonly used antimalarial drugs. It is difficult for non-experts to morphologically distinguish between falciparum malaria and non-falciparum malaria. Using tagging liposomes which can bind to red cells which are infected with falciparum malaria would enable a technician to identify the infection. The antibodies on the liposomes are specific to a red cell membrane surface antigen unique to falciparum-infected red cells.

Since many changes and variations of the disclosed embodiment of the invention may be made without departing from the inventive concept, it is not intended to limit the invention otherwise than as required by the appended claims.

What is claimed is:

1. A method for assaying a biological fluid sample for the presence of a target component in the sample, said method comprising the steps of:

a) providing a plurality of liposome vesicles having an antibody attached to an external surface of said vesicles, said antibody being specific to a surface antigen on said target component; said vesicles having an incorporated marker material and/or carrier which renders said vesicles detectable in the biological fluid sample, and said marker material and/or carrier imparting to said vesicles a specific gravity which is different from the specific gravity of said target component;

b) adding said vesicles to the fluid sample to form a mixture thereof;

c) centrifuging the mixture to gravimetrically separate any liposome-target combinations into a distinct band in the mixture; and d) identifying and/or quantifying said distinct band in the centrifuged mixture.

2. A method for assaying a blood sample for the presence of T-lymphocytes or their subsets in the sample, said method comprising the steps of:

a) providing a plurality of liposome vesicles having an antibody attached to an external surface of said vesicles, said antibody being specific to a surface antigen on said T-lymphocytes or subsets; said vesicles having an incorporated marker material which renders said vesicles detectable in the sample, and said marker material imparting to said vesicles a specific gravity which is different from the specific gravity of said T-lymphocytes or subsets;

b) adding said vesicles to the sample to form a mixture thereof;

c) centrifuging the mixture to gravimetrically separate any liposome-T-lymphocyte or subset combinations into a distinct band in the mixture; and d) identifying and/or quantifying said distinct band in the centrifuged mixture.

3. A method for assaying a blood sample for the presence of a target constituent in the sample, said method comprising the steps of:

a) providing a plurality of liposome vesicles having an antibody attached to an external surface of said vesicles, said antibody being specific to a surface antigen on said target constituent; said vesicles having an incorporated marker material which renders said vesicles detectable in the sample, and said marker material imparting to said vesicles a specific gravity which is different from the specific gravity of said target constituent;

b) adding said vesicles to the sample to form a mixture thereof;

c) centrifuging the mixture to gravimetrically separate any liposome-target constituent combinations into a distinct band in the mixture; and d) identifying and/or quantifying said distinct band in the centrifuged mixture.

4. The method of claim 3 wherein said target constituent is a particular type of blood cell.

5. A method for assaying a biological fluid sample for the presence of at least two target components in the sample, said method comprising the steps of:

a) providing a plurality of first liposome vesicles having a first antibody attached to an external surface of said first vesicles, said first antibody being specific to a surface antigen on one of said target components; said first vesicles having an incorporated first marker material which renders said first vesicles detectable in the biological fluid sample, and said first marker material imparting to said first vesicles a first specific gravity which is different from the specific gravity of said one of said target components;

b) providing a plurality of second liposome vesicles having a second antibody attached to an external surface of said second vesicles, said second antibody being specific to a surface antigen on another of said target components; said second vesicles having an incorporated second marker material which renders said second vesicles detectable in the biological fluid sample, and said second marker material imparting to said second vesicles a specific gravity which is different from the specific gravity of said another of said target components, and which is also different from said first specific gravity;

c) adding said vesicles to the fluid sample to form a mixture thereof;

d) centrifuging the mixture to gravimetrically separate any liposome-target combinations into distinct bands in the mixture; and e) identifying and/or quantifying said distinct bands in the centrifuged mixture.

* * * * *